(12) United States Patent
Byrne

(10) Patent No.: US 6,210,322 B1
(45) Date of Patent: Apr. 3, 2001

(54) ADAPTER FOR THE CONNECTION OF A WATER BOTTLE TO AN ENDOSCOPE

(76) Inventor: Donny M. Byrne, 4074 Whipporwill Rd., Conroe, TX (US) 77303

( * ) Notice: Subject to any disclaimer, the term of this patent is extended or adjusted under 35 U.S.C. 154(b) by 0 days.

(21) Appl. No.: 09/166,731

(22) Filed: Oct. 5, 1998

Related U.S. Application Data (60) Provisional application No. 60/078,668, filed on Mar. 20, 1998, and provisional application No. 60/074,073, filed on Feb. 9, 1998, now abandoned.

(51) Int. Cl.[7] .................................................. A61B 1/015
(52) U.S. Cl. ............................................................. 600/158
(58) Field of Search ................................... 600/156, 158, 600/159; 604/257, 405, 533

(56) References Cited

U.S. PATENT DOCUMENTS

| | | | |
|---|---|---|---|
| 4,301,799 | * | 11/1981 | Pope, Jr. et al. .................... 604/405 |
| 4,552,130 | * | 11/1985 | Kinoshita .............................. 600/158 |
| 4,667,655 | * | 5/1987 | Ogiu et al. ............................ 600/132 |
| 4,760,838 | * | 8/1988 | Fukuda .................................. 600/158 |
| 5,133,336 | * | 7/1992 | Savitt et al. .......................... 600/132 |
| 5,195,664 | * | 3/1993 | Rhea ................................... 222/464.4 |
| 5,297,537 | * | 3/1994 | Savitt et al. .......................... 600/158 |
| 5,437,654 | * | 8/1995 | McVay .................................. 604/403 |
| 5,707,351 | * | 1/1998 | Dorsey, III .............................. 604/30 |
| 5,807,313 | * | 9/1998 | Delk et al. .............................. 604/35 |
| 5,830,128 | * | 11/1998 | Tanaka .................................. 600/158 |

\* cited by examiner

*Primary Examiner*—John P. Leubecker
(74) *Attorney, Agent, or Firm*—Harrison & Egbert

(57) ABSTRACT

An adapter for a disposable water bottle for an endoscope having a cap with threads suitable for attachment to threads on a neck of the water bottle, an outer tube affixed to an opening in the cap, and an inner tube extending through the outer tube. The inner tube forms an air passing annulus on an interior of the outer tube. The inner tube extends outwardly of an end of the outer tube and through the opening in the cap. A fitting is non-removably affixed to an end of the inner and outer tubes opposite the cap. The fitting is adapted for attachment to air and water connections of the endoscope. The outer tube, the inner tube and the cap are formed of a polymeric material.

9 Claims, 6 Drawing Sheets

ADAPTER FOR THE CONNECTION OF A WATER BOTTLE TO AN ENDOSCOPE

RELATED APPLICATIONS

The present utility patent application claims the benefit of a prior filed U.S. Provisional Patent Application Ser. No. 60/078,668, filed on Mar. 20, 1998 and U.S. Provisional Application Ser. No. 60/074,073, filed on Feb. 9, 1998, now abandoned.

TECHNICAL FIELD

The present invention relates to endoscopic systems. More particularly, the present invention relates to water bottles as used with endoscopic systems. Furthermore, the present invention relates to delivery tubes for passing the water from a water bottle to the optical head of the endoscopic instrument.

BACKGROUND ART

Endoscopic instruments have been developed to provide surgeons with an internal view of the organ or body passage requiring treatment. Such endoscopes typically have channels through which a miniaturized forceps, commonly called flexible instruments, are inserted and advanced. The endoscope assembly includes an elongated flexible cable equipped at one end with an eyepiece or other viewing means and at the other end with an optical head. Only the head is directly and externally connected to the instrument. The cable transmits images or image-producing signals from the illuminated operative site to the viewing means so that the surgeon will have visual confirmation of the action of the instrument's working end. A coherent optic bundle extends from the head and through the flexible cable through the eyepiece for providing the surgeon with visual confirmation of the instrument's tip or jaw action. The illuminating means may take the form a light-transmitting waveguide extending through the cable to illuminate the operative area. The waveguide is connected at its proximal end to a suitable high-intensity light source. The cable also provides a flow passage for the delivery of fluid (liquid or gas) for irrigation or other purposes. Typically, the flow passage and the illuminating means are disposed on opposite sides of the coherent image-transmitting waveguide. In conventional practice, it is necessary to provide the optic head with a flow of sterile water. The passage of the sterile water across the optic head prevents the buildup of materials on the optic head. This flow of water operates, in a sense, like a windshield wiper/washer assembly.

In normal practice, the endoscopic instrument has a control body which is connected by a light guide tube to a light guide connector. The connector will include a plurality of connectors that can suitably receive various fittings. For example, the light guide connector can include a connector orifice that receives a grounding lug, a suction port, an air inlet, and a water inlet. As such, the air and water are delivered through the light guide connector, through the light guide tube and into the control body. Alternatively, the control body can also include a water port so as to allow water to be directly provided to the control body. Suitable valves are provided on the control body so as to control the flow of water through the control body and over the optic head of the instrument.

Unfortunately, there is usually a great expense associated with the delivery of such sterile water to the control body. In past practice, the sterile water has been provided from a water bottle that is directly connected to a tube. The tube will have a fitting at one end so as to allow the tube to be connected to the air/water inlet of the light guide connector or to the auxiliary water port on the control body. Typically., the fitting will include an inner tube and an outer tube. The outer tube extends into the water bottle. The outer tube is connected to the cap of the water bottle. In normal practice, air is delivered through the area between the inner tube and the outer tube so as to pressurize the interior of the water container. This will force water to flow through the tube and into the endoscope at a desired rate.

After usage, the water bottle, the tubing, and the associated fittings are sterilized. This creates a considerable wastefull expense to the hospital. If the water is sterilized, there is a considerable labor expense associated with the autoclaving of the bottle. There is also the possibility of residual contaminants residing in the area of connection between the tubes and the bottle.

In the normal hospital environment, sterile water is conventionally provided in one liter bottles. Virtually all of the bottles have the same size of threaded opening. These water bottles are very different, in configuration, from the water containers associated with the prior art water delivery systems for the endoscopic instrument. Typically, existing one liter water bottles in hospitals will be sealed closed by threadedly connecting the interior threads of a cap over the exterior threads on the neck of the bottle.

Figures 5, 6, 7:
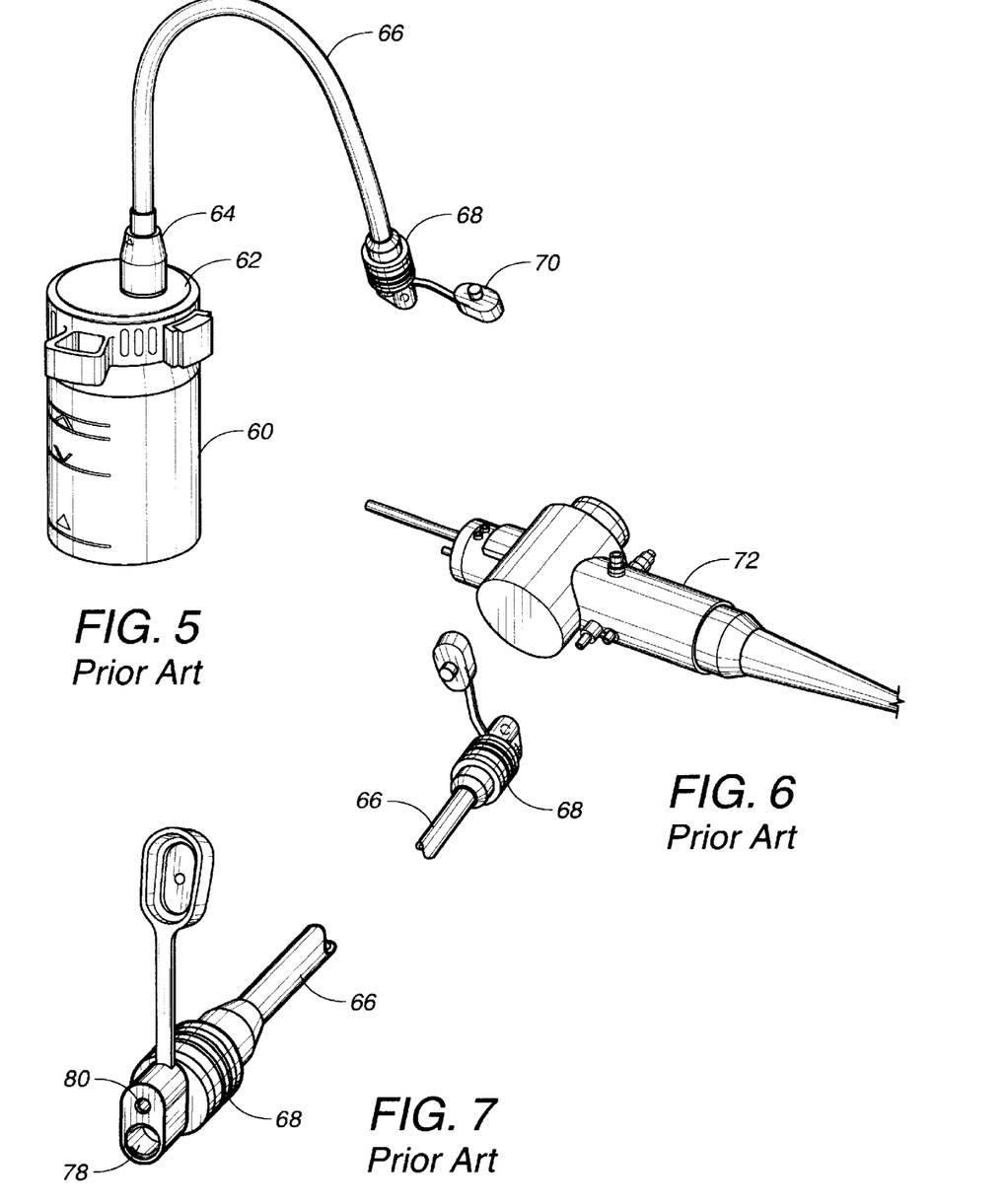
FIG. 5 is a perspective view of a prior art water container, and associated fittings, as used with the 140 series of endoscopes.
FIG. 6 is a perspective view showing the joining of the metal fitting of the water container of FIG. 5 with the 140 series of endoscopes.
FIG. 7 is a perspective end view of the metal end fitting as used with the water container of FIG. 5.

A new system of endoscopes has been provided which has an unusual adapter for connecting the water bottle to the endoscope. The new 140 series of endoscopes has a pair of female fittings on the adapter for the delivery of air and water to the male fittings of the endoscope. FIGS. 5–7 show this existing prior art system of connection to the 140 series endoscopes.

In FIG. 5, it can be seen that there is a specialized water bottle 60 which has a lid 62 having a tube connection 64 thereon. The tube connection 64 connects to tube 66 which extends to the metal tip 68. A cleaning cap is provided on the metal tip 68. The tube 66 and the tip 68 serve to deliver sterile water from the container 60 to the endoscope.

FIG. 6 shows the 140 series endoscope 72 having a water supply connector 74 and an air connector 76. The water supply connector 74 is a male connector. The air connector 76 is also a male connector. Connector 74 serves to pass water from the water bottle to the interior of endoscope 72, connector 76 serves to pass air from the endoscope to the water bottle.

FIG. 7 shows an end view of the metal tip 68. As can be seen, the metal tip 68 has a female water connector 78 and a female air connector 80. The female water connector 78 is suitable for connection to the male water connector 74 on the endoscope 72. The female air connector 80 is suitable for connection to the male air connector 76 on the endoscope 72.

The new configuration of water container system as shown in FIGS. 5–7 serves to make obsolete the existing expensive water containers and associated tubing and adapters which are used for other endoscopes. As such, as hospitals purchase the new 140 series endoscope 72, they are required to also purchase the new water container 60, the new tubing 66, and the new metal tip 68. The water containers that have been used for prior endoscope systems must also be supplied for any prior endoscope systems that the hospital may have in use. As a result, hospitals are required to manage and maintain inventory of water bottles such as those shown in FIGS. 5–7 and also water containers for their existing endoscope systems. As such, a need has developed so as to allow for the standardization of the water containers for the various endoscope systems which are offered. Any standardization that can be achieved will eliminate the need to maintain inventory for each of the various types of endoscopes which a hospital employs.

It is an object of the present invention to provide a water bottle adapter for an endoscopic instrument which eliminates the need for the specialized water bottle.

It is another object of the present invention to provide such an adapter which can be used with conventional one liter water bottles existing in the hospital environment.

It is a further object of the present invention to provide such adapter which does not require the disposal or sterilizing of both the adapter and the water container.

It is a further object of the present invention to provide such an adapter which is easy to use, which significantly reduces costs, and is easy to manufacture.

It is a further object of the present invention to provide an adapter which allows for the water bottles to be properly connected to the new 140 series of endoscopes.

It is still another object of the present invention to provide an adapter which allows for the water container systems of existing endoscopes to be adapted and fitted to the new 140 series of endoscopes.

It is a further object of the present invention to provide an adapter which allows for connection to the water bottle which assures that the water transmitting tube has an end residing at the bottom of the water bottle.

It is still a further object of the present invention to provide an adapter which is transparent for easy viewing of the interior of the adapter.

It is a further object of the present invention to minimize costs associated with the sterilizing of existing water bottles.

These and other objects and advantages of the present invention will become apparent from a reading of the attached specification and the appended claims.

SUMMARY OF THE INVENTION

The present invention is a water bottle adapter for use with an endoscopic instrument. The water bottle adapter of the present invention includes an inner tube, an outer tube, and a plastic cap which is secured to the outer tube and through which the inner tube extends. The plastic cap has interior threads that are adapted to engage the exterior threads on the neck of existing one liter sterile water bottles. In actual use, the plastic cap is to be secured onto such threaded neck of the water bottles such that the inner tube will extend into the interior of such water bottles. A fitting is affixed to the end of the inner tube and the outer tube opposite the cap. The fitting allows for the attachment of the inner and outer tubes to the endoscopic instrument.

Both the inner tube and the outer tube are formed of an elastomeric or plastic material. An air passing annulus is defined between the exterior surface of the inner tube and the interior surface of the outer tube. As such, this forms an annular air passageway such that the air can pass through the fitting and into this annular passageway. The flow of water into the end of the inner tube within the existing hospital water bottle is controlled by the amount of air flow that will pass through this annular passageway. The water will flow more quickly from the water bottle into the inner tube when a greater amount of air pressure is exerted into the interior of the water bottle through the annular passageway. An anchor member is affixed to the end of the inner tube so as to assure that the end of the inner tube resides at the bottom of the water bottle. Both the inner and outer tubes are transparent.

The plastic cap is secured onto the water bottle such that the annular passageway between the inner tube and the outer tube will flow into the interior of the water bottle.

The present invention provides an adapter for such a water bottle which allows the water bottle to be easily connected to the new 140 series of endoscopes. These endoscopes are of the type having a male air fitting and a male water fitting. In particular, the present invention is an adapter which includes an adapter body which has an air passageway formed therein. The air passageway is formed through the body so as to communicate between a female connector at one end and to the air passageway between the inner tube and the outer tube. The body also includes a water passageway which has a female connector at one end. The female connector is suitable for joining to the male water connector of the 140 series of endoscopes. The water passageway will extend from the female water connector through the interior of the body so as to open to the interior of the inner tube. As such, water will flow properly from the water bottle, through the interior of the inner tube, through the passageway in the body, into the endoscope through the connection o f the female water connector to the male water connector. The body with the female air connector and the female water connector can be utilized whenever it is necessary to connect the water bottle of the present invention to the 140 series of endoscopes.

DETAILED DESCRIPTION OF THE INVENTION

Figure 1:
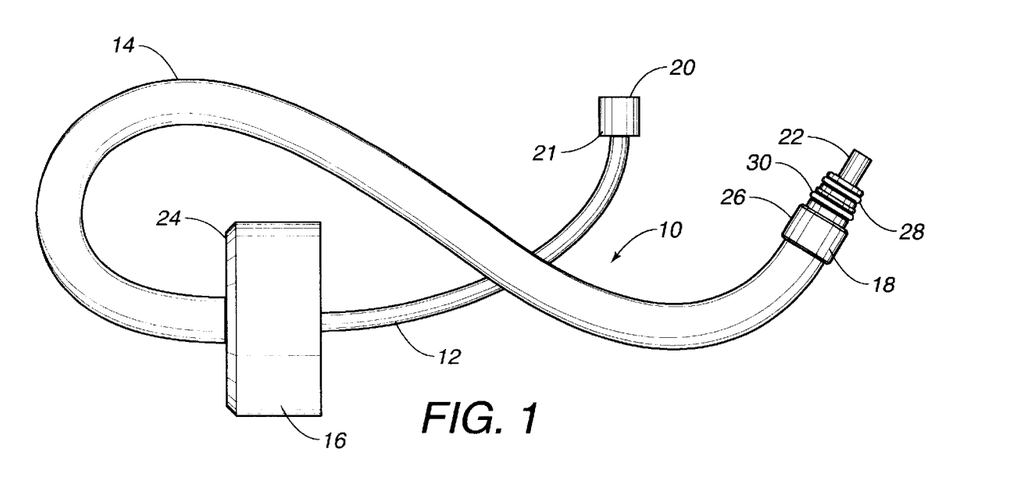
FIG. 1 is a side elevational view of the water bottle adapter in accordance with the preferred embodiment of the present invention.

Referring to FIG. 1, there is shown at 10 the water bottle adapter in accordance with the preferred embodiment of the present invention. The water bottle adapter 10 includes an inner tube 12, an outer tube 14, a bottle cap 16, and a fitting 18. The inner tube 12 extends outwardly of the bottle cap 16 and has an opening at end 20. In normal use, the inner tube 12 will extend into the interior of the water bottle. The bottle cap 16 will be threadedly secured to the threaded neck of the water bottle. The inner tube 12 will extend through the cap 16, through the interior of the outer tube 14, and will terminate at the fitting 18. The inner tube 12 is made of a plastic or elastomeric material. A nozzle 22 is provided at the end of the fitting 18 so as to allow for the water from the inner tube 12 to be dispensed therefrom. The end 20 has a metallic anchor member 21 affixed thereto.

The outer tube 14 is also a flexible plastic or elastomeric tube. The outer tube 14 will extend from the back 24 of the bottle cap 16 and will terminate at the fitting 18. As will be described hereinafter, an annular passageway on the interior of the outer tube 14 is formed by the exterior of the inner tube 12 and the interior of the outer tube 14. This annulus will allow for the passage of air from the fitting 18 to the interior of the cap 16 as it is secured to a water bottle. As such, the necessary "pumping" effect can be achieved so as to allow for the passage of water into the end 20 of the inner tube 12. The outer tube 14 is secured to an outer tube fitting 26. A pair of O-rings 28 and 30 are provided on the exterior of the fitting 18 so as to allow the fitting 18 to be properly secured to the endoscopic instrument in the manner of conventional water bottle tubes.

In FIG. 1, it can be seen that the anchor member 21 is affixed to the end 20 of the inner tube 12. The anchor member 21 serves to assures that the end 20 of the inner tube 12 will reside adjacent to the bottom of the sterile water bottle. Conventionally, when the tubing 12 is formed, it will have a "memory" such that the tubing 12 will tend to recoil upwardly within the water bottle. As such, the end 20 of the inner tube cannot extend to the very bottom of the water bottle. As a result, not all of the water within the water bottle will be available for use. However, with the attachment of the anchor member 21 to the end 20 of the inner tube 12, a sufficient weight is achieved so as to overcome this "memory" of the inner tube 12. So as to avoid this connection, the anchor member 21 is ultraviolet glued to the ends 20 of the inner tube 12. Similarly, the fitting 18 will be ultraviolet affixed to the end of the outer tube 14 and to the inner tube therewithin. The cap 16 has inner threads which are particularly adapted for joining with the threads of the most popular available configurations of water bottles.

Figure 2:
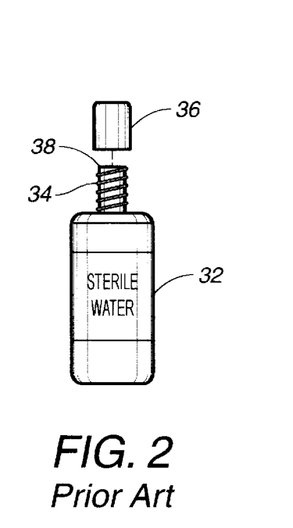
FIG. 2 is an exploded isolated view of an existing sterile water bottle.

FIG. 2 is an isolated view of a water bottle 32. The water bottle 32 is a one liter water bottle of a conventional type used in hospitals. The water bottle 32 is conventionally filled with sterile water. It is necessary to use sterile water since such water will pass to the interior of the human body during the process of cleaning the optic head of the endoscopic instrument. The water bottle 32 has an externally threaded neck 34. In normal use, a cap 36 is threadedly secured to the threaded neck 34 so as to prevent leakage or dispensing of the water from the interior of the bottle 32.

Figure 3:
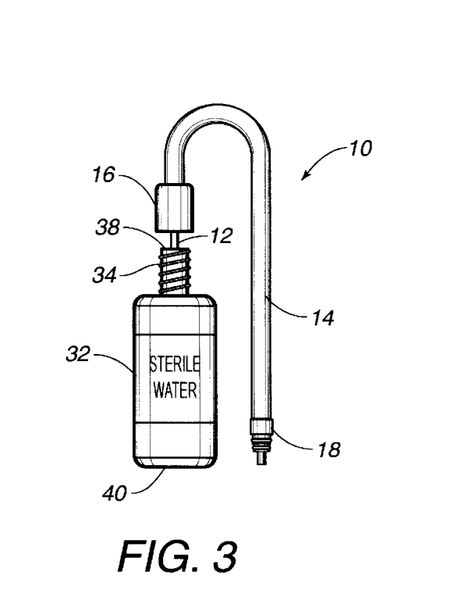
FIG. 3 shows the assembly of the water bottle adapter of the present invention with the existing hospital water bottle.

So as to effect the use of the adapter 10 of the present invention, it is necessary for the cap 36 to be threadedly removed from the exterior of the neck 34 of water bottle 32. The next step in the process of the present invention is shown in FIG. 3. As can be seen in FIG. 3, the inner tube 12 will be inserted into the opening 38 at the top of the neck 34 of the water bottle 32. Inner tube 12 will extend down into the interior of the water bottle 32 such that the end 20 of the inner tube 12 will reside adjacent to the bottom 40 of the water bottle 32. The use of anchor member 21 assures that the inner tube 12 will reside at the bottom 40 of the water bottle 32.

Once the inner tube 12 is inserted through the opening 34 of the water bottle 32, the bottle cap 16 will be moved downwardly to the opening 38 on the neck 34. The cap 36 can be rotated so as to threadedly secure the cap 16 around the exterior surface of the neck 34. Once the cap 36 is properly secured in its position, the adapter 10 is ready for attachment to the endoscopic instrument. The fitting end 18 is located at the opposite end of the outer tube 14 so as to allow for a quick connection to the endoscopic instrument.

Figure 4:
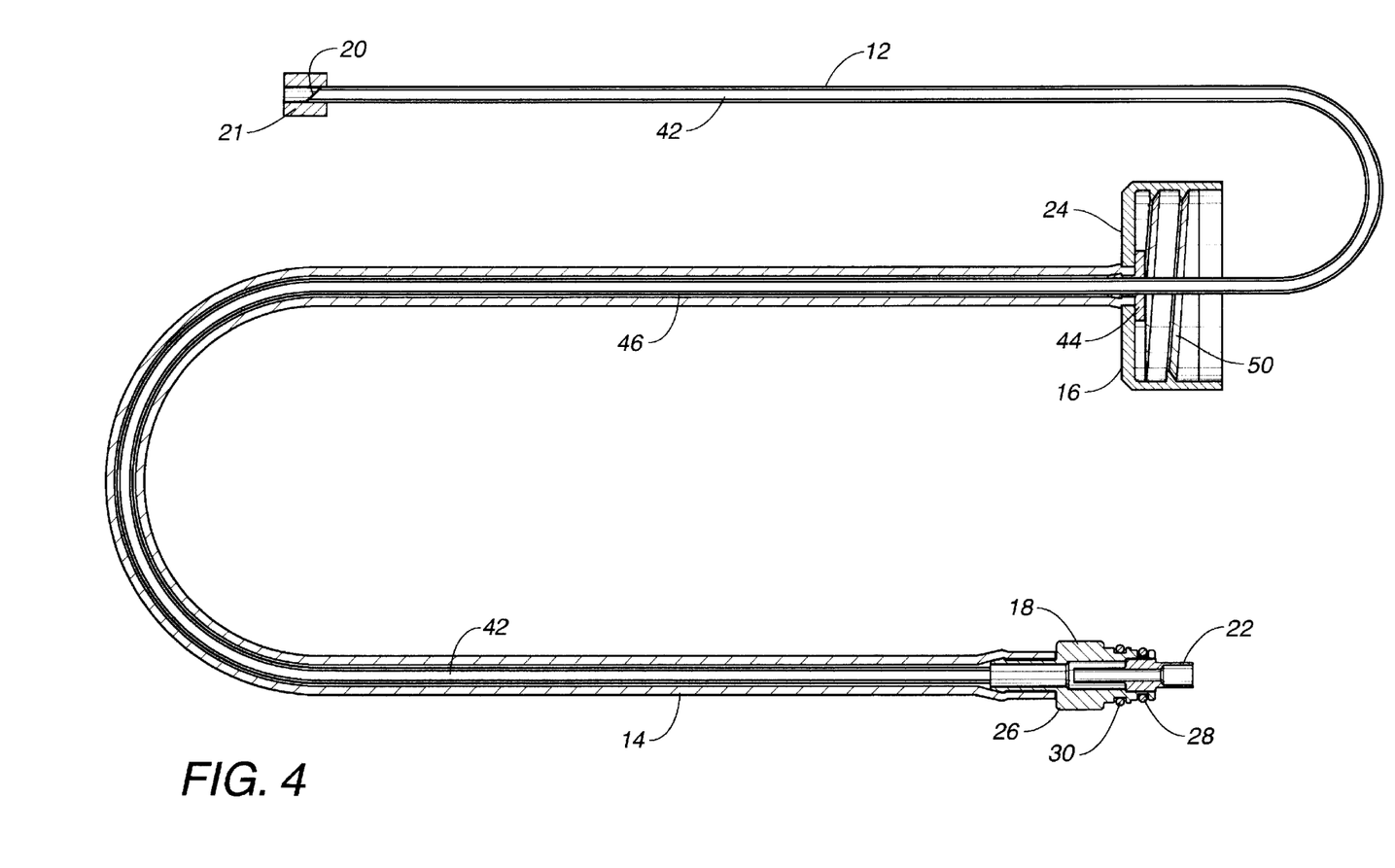
FIG. 4 is a cross-sectional view of the water bottle adapter in accordance with the preferred embodiment of the present invention.

FIG. 4 shows the interior arrangement of the inner tube 12, the outer tube 14, the cap 36 and the fitting 18. As can be seen, the inner tube 12 has an opening at end 20. Anchor member 21 is affixed to end 20. An interior passageway 42 extends through the length of the inner tube 12. This interior passageway, along with the inner tube 12, terminates at the inner tube fitting 22 at the distal end of the fitting 18.

The outer tube 14 has one end which is secured to the back 24 of the cap 36. A suitable fitting 44 allows the passage of the inner tube 12 through the interior of the outer tube 14. An annular passageway 46 is then formed between the inner surface of the outer tube 14 and the outer surface of the inner tube 12. The fitting 44 is positioned so as to allow air passing through this annular passageway 46 to enter the interior of the bottle onto which the cap 16 is secured.

The outer tube 14 is affixed to the outer tube fitting 26. Suitable O-ring seals 28 and 30 fit around the exterior of the fitting 18. In this manner, air is allowed to enter through the fitting 18 and through the annular passageway 46 between the inner tube 12 and the outer tube 14.

The cap 36 has interior threads 50 that are sized to fit on the various shapes and sizes of exterior threads on the neck 34 of the water bottle 32.

In actual use, a controlled flow of air is maintained through the air passing annulus 46 so as to control the flow of water through the interior 42 of the inner tube 12. If more water flow is desired, then greater air pressure is delivered through the annular passageway 46 to the interior of the water bottle 32. If less water flow is desired, then less air pressure is applied.

Figure 8:
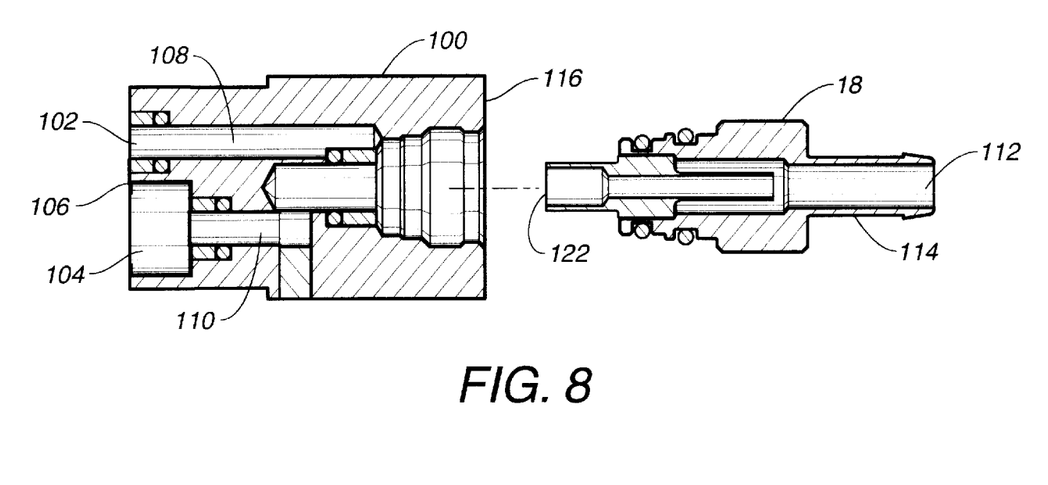
FIG. 8 is a cross-sectional view of the adapter body of the present invention as used with the fitting to the water bottle of the present invention.

FIG. 8 illustrates how the fitting 18 can be connected to the new 140 series of endoscopes. So as to allow the fitting 18 to be properly connected to the 140 series of endoscopes, it is necessary to employ adapter body 100. The adapter body 100 has a female air connector 102 and a female water connector 104 at end 106 of the adapter body 100. The female air connector 102 is sized and shaped so as to fit onto the male air connector 76 of the endoscope 72. Similarly, the female water connector 104 is sized and shaped so as to receive the male water connector 74 of endoscope 72. In general, the female connectors 102 and 104 are suitable for attaching to the male connectors of the 140 series of endoscopes.

An air passageway 108 will extend through the adapter body 100 so as to open, on the interior of the adapter body 100, and then so as to pass into the annular area between the outer tube and the inner tube of the water bottle system. Similarly, a water channel 110 is provided on the interior of the adapter body 100 so as to allow water to pass into the female water connector 104 from the interior of the adapter body 100 and from the interior 112 of the tube 114. As such, this allows water to be delivered to the endoscope from the water bottle. Suitable O-ring seals are incorporated throughout the adapter body 100 so as to achieve a strong liquid and airtight seal between the fitting 18 and the interior of the adapter body 100. Additionally, appropriate O-ring seals are provided on the female air connector 102 and the female water connector 104 so as to achieve a strong water and airtight fitting between the male and female connectors.

Figure 9:
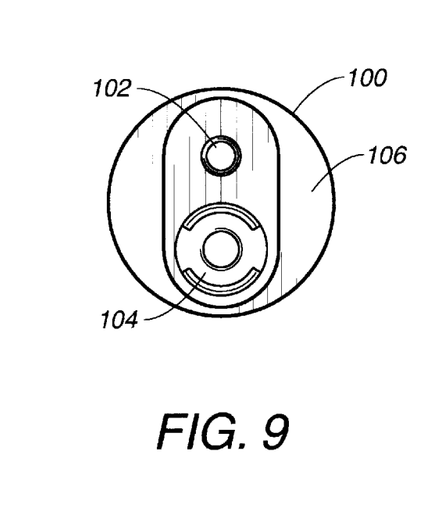
FIG. 9 is an end view of the female connectors as used on the adapter body o f the present invention.

FIG. 9 is a view of the end 106 of the adapter body 100. As can be seen, there is a small opening which illustrates the female air connector 102. A larger opening is provided below the female air connector 102 so as to illustrate the female water connector 104. As can be seen, the end 106 with its female air connector 102 and female water connector 104 has a similar configuration as the end view of the metal tip 68 as shown in FIG. 7.

Figure 10:
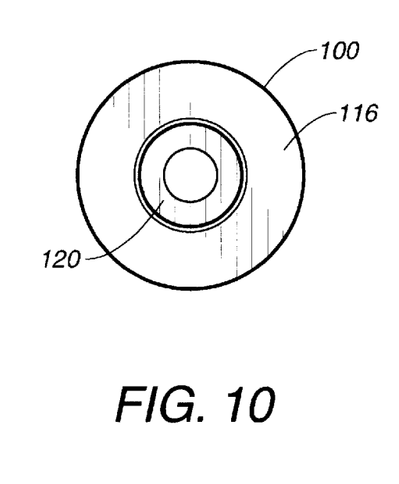
FIG. 10 is an opposite end view of the adapter body of the present invention.

FIG. 10 is a view of end 116 of the adapter body 100. An opening 120 is provided so as to allow for the entry of the water passageway 122 of the fitting 18.

Figure 11:
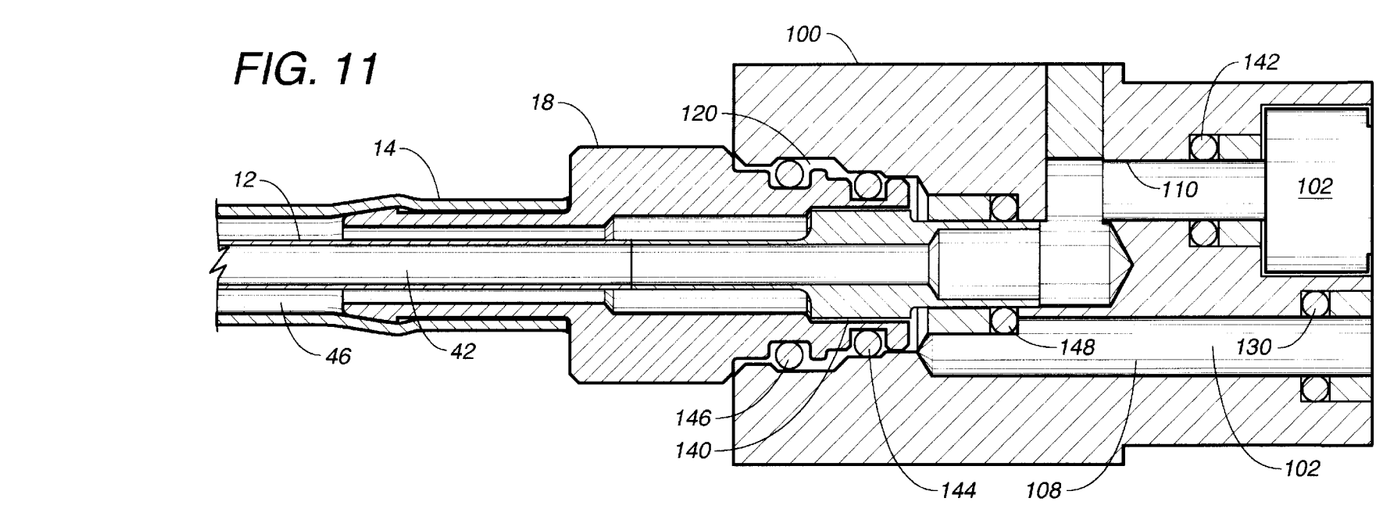
FIG. 11 is a cross-sectional view showing the joining of the adapter body with the fitting for the water bottle of the present invention.

FIG. 11 illustrates the manner in which the fitting 18 is connected onto the interior of the adapter body 100. Initially, it can be seen that the adapter body 100 has the female water connector 104 and the female air connector 102 at one end. A O-ring seal 130 is provided on the interior of the female air connector 102 so as to create a strong airtight seal with the exterior surface of the male air connector 76 of endoscope 72.

As was described herein previously, air will flow through the annular space 46 between the inner tube 12 and the outer tube 14. In the present invention, air can flow through the air passageway 108 through air channel 140 and into the annular space 46 between the inner tube 12 and the outer tube 14.

The female water connector 104 has a suitable size for receiving the exterior surface of the male water connector 74 of endoscope 72. A suitable O-ring seal 142 is provided on the water passageway 110 so as to create a water-tight seal between the exterior surface of the male water connector 74 and the inner surface of water passageway 110. Water will flow through water passageway 110 through the interior of the adapter body 100 so as to enter the water outlet 22. Water outlet 22 communicates with the interior 42 of the inner tube 12 so as to allow for the delivery of water from the water bottle to the endoscope instrument.

It can be seen that the fitting 18 is appropriately received within the opening 120 of the adapter body 100. O-ring seals 144 and 146 are provided on the exterior surface of the fitting 118 so as to create the necessary air and water-tight seal between the exterior surface of the fitting 18 and the interior surface of the opening 120. Another O-ring seal 148 is provided adjacent to the water outlet 22 so as to create a water-tight seal.

As can be seen in FIGS. 8–11, the present invention provides an adapter body 100 which allows for the receipt of a fitting 18 for the water bottle system of the present invention so as to allow it to be connected to the new 140 series of endoscopes. Additionally, the present invention provides an adapter body 100 which allows existing expensive water bottles which have been used for prior endoscope systems to also be used with the new 140 series of endoscopes. As a result, it is no longer necessary to purchase separate water bottles for the various endoscopes. Even though a hospital purchases the new 140 series of endoscopes, they can continue to use the existing equipment.

Since the cap 36 is adapted to standard one liter hospital water bottles, there is no need to purchase the specialized water bottle associated with existing water delivery systems for endoscopic instruments. After actual use, the adapter 10 can be disposed. Since there is no direct contact between the bodily fluids of the patient and the interior of the water bottle, the water bottle can be sterilized and reused or disposed of. The elimination of the specialized water container associated with existing water flow delivery systems for endoscopic instruments will greatly reduce the cost of such adapters.

Figure 12:
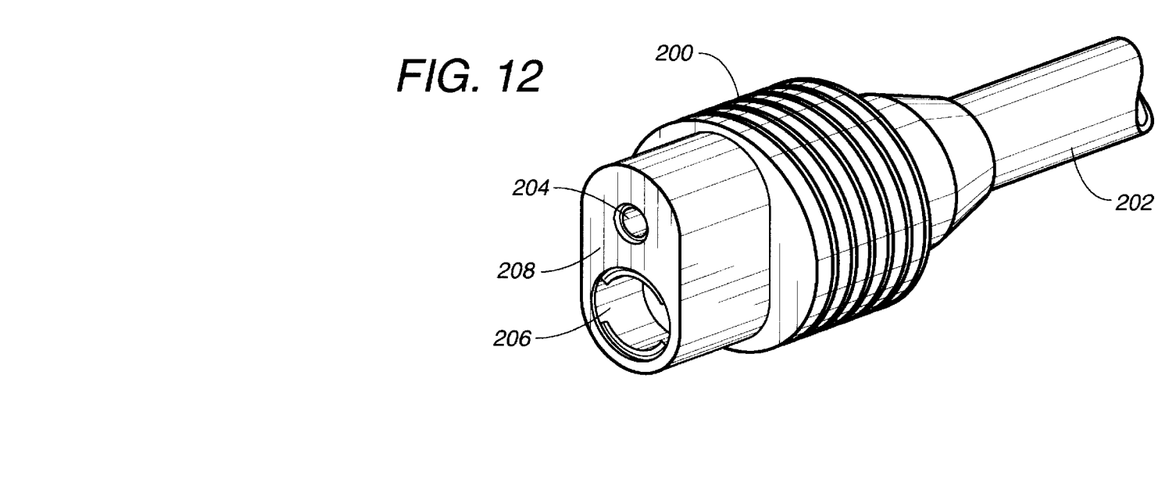
FIG. 12 is a perspective end view of the adapter body as permanently affixed to the end of the tubes.

FIG. 12 shows an alternative form of the embodiment shown in FIGS. 8–11. In FIG. 12, it can be seen that the adapter body 200 is permanently affixed to the tubing 202. As can be seen, the air connector female fitting 204 and the water connector female fitting 206 extend outwardly form the end 208 of the adapter body 200. In this embodiment of the present invention, the adapter body 200 is directly affixed to the end of tubing 202 without the use of the fitting 18. Alternatively, the adapter body 200 can be permanently affixed onto the fitting 18. In this embodiment of the present invention, the adapter body 200, along with the tubing 202, is formed of a transparent material. As such, visual observation can be used so as to detect any contaminants which may occur within the adapter body 200 or the tubing 202. Since the adapter body 200 is formed of a disposable polymeric material, the adapter body 200 and the tubing 202 can be disposed of after use. No sterilizing or autoclaving is required.

Figure 13:
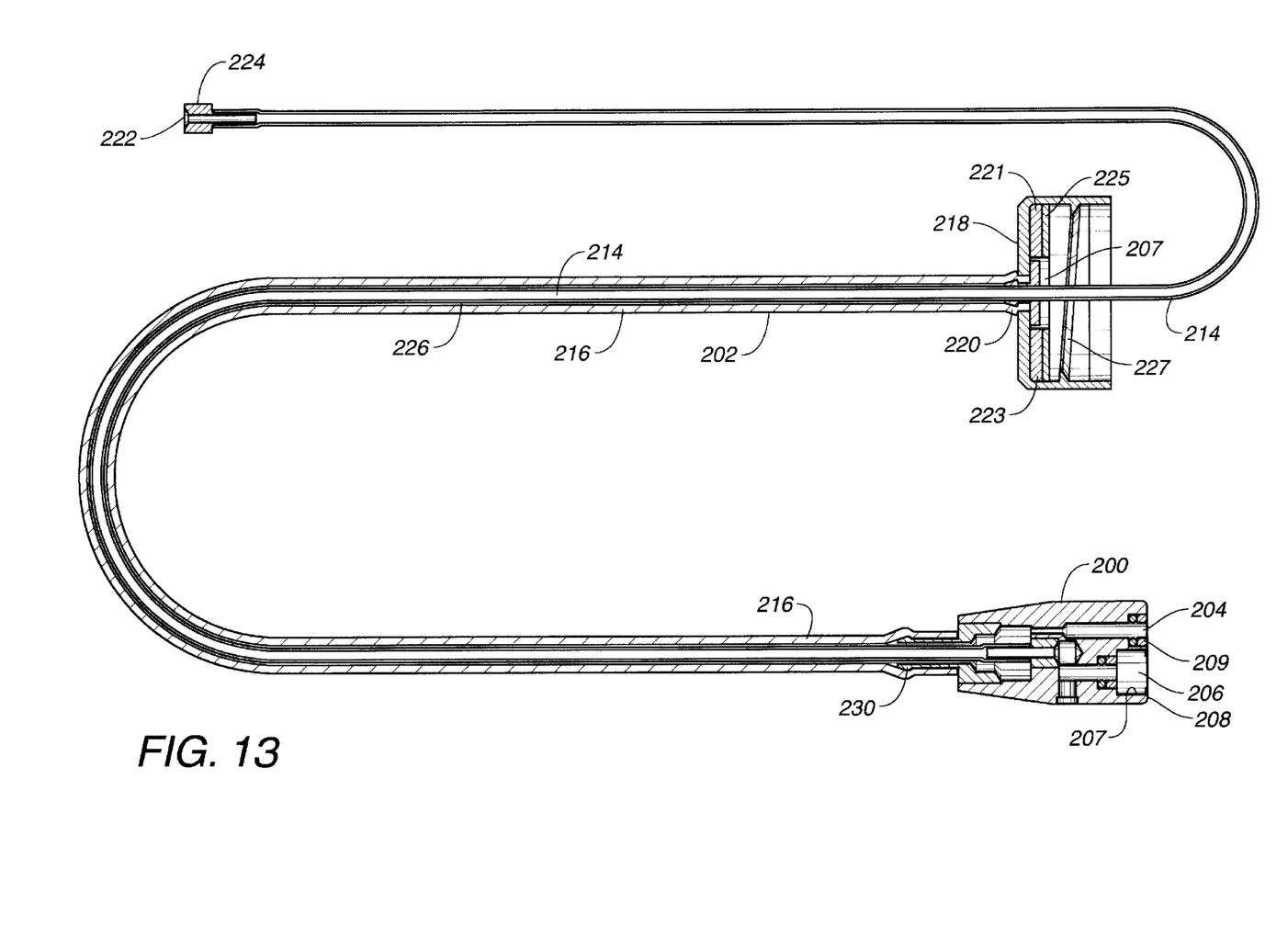
FIG. 13 is a cross-sectional view of the adapter as permanently affixed to the end of the tube.

FIG. 13 is a cross-sectional view of the complete apparatus in accordance with the teachings of FIG. 12. In FIG. 13, it can be seen that the adapter body 200 is connected to tubing 202. The tubing 202 has an inner tube 214 and an outer tube 216. The outer tube 216 is connected to the opening in the cap 218. Cap 218 is adapted for connection to existing one liter water bottles. The inner tube 214 will extend through the opening 220 in the cap 218 so as to extend to end 222. Ends 222 has a metallic anchor member 224 affixed thereto. The air passing annulus 226 is formed in the area between the inner tube 216 and the inner tube 214.

It can be seen that the adapter body 200 has female air passageway 204 and female water passageway 206 opening at end 208 of the adapter body 200. As can be seen, the female connector 204 has a channel which extends through the adapter body 200 so as to allow air to be emitted into the air-passing annulus 226. Similarly, the female water connector 206 is suitably connected to the interior of the inner tube 214 so as to allow water to pass therethrough. The outer tubing 216 is secured over a male connector 230 at the opposite end of the adapter body 200 from the end 208. The interior of the outer tube 226 can be ultraviolet sealed onto the male connector 230. As such, the adapter body 200 is non-removably affixed to the tubing 202.

The foregoing disclosure and description of the invention is illustrative and explanatory thereof. Various changes in the details of the illustrated apparatus may be made within the scope of the appended claims without departing from the true spirit of the invention. The present invention should only be limited by the following claims and their legal equivalents.

I claim:

1. An adapter apparatus for a disposable water bottle for an endoscope comprising:

a cap having threads suitable for attachment to threads on the neck of a water bottle;

an outer tube affixed to an opening in said cap;

an inner tube extending through said outer tube, said inner tube forming an air passing annulus on an interior of said outer tube, said inner tube extending outwardly of an end of said outer tube and through said opening in said cap;

a fitting non-removably affixed to an end of said inner and outer tubes opposite said cap; and an adapter body removably affixed to said fitting, said adapter member having a first female connector and a second female connector, said adapter body having a receptacle formed at one end thereof, said adapter body having an opposite end for connection to an air line and a water line of an endoscope, said fitting affixed in fluid-tight relationship within said receptacle of said adapter body, each of said first and second female connectors opening in side-by-side spaced relationship at said opposite end of said adapter body, said adapter body having a water channel communicating with said second female connector and extending through said adapter body so as to open at said one end of said adapter body and connected with an interior of said inner tube through said fitting, said adapter body having an air passing channel communicating with said first female connector and extending through said adapter body so as to open at said one end of said adapter body and connect with said air passing annulus, said inner tube being interior of said air passing annulus within said fitting, said adapter body being formed of a generally transparent rigid polymeric material.

2. The adapter of claim 1, said outer tube having an outer surface affixed in air-tight relationship with said opening of said cap.

3. The adapter of claim 1, said inner tube extending continuously through said outer tube.

4. The adapter of claim 1, said outer tube, said inner tube and said cap being formed of a polymeric material.

5. The adapter of claim 1, said inner tube having an anchor member affixed to an end of said inner tube extending outwardly from said outer tube.

6. The adapter of claim 5, said anchor member being adhesively affixed to said inner tube, said fitting being adhesively affixed to said inner and outer tubes.

7. The adapter of claim 6, said anchor member being ultraviolet glued to said inner tube, said fitting being ultraviolet glued to said inner and outer tubes.

8. The adapter of claim 1, said inner tube having a length greater than a length of said outer tube.

9. The adapter of claim 1, said threads of said cap being interior threads adapted for forming an air-tight seal with the neck of the water bottle.

* * * * *